Figure 1:
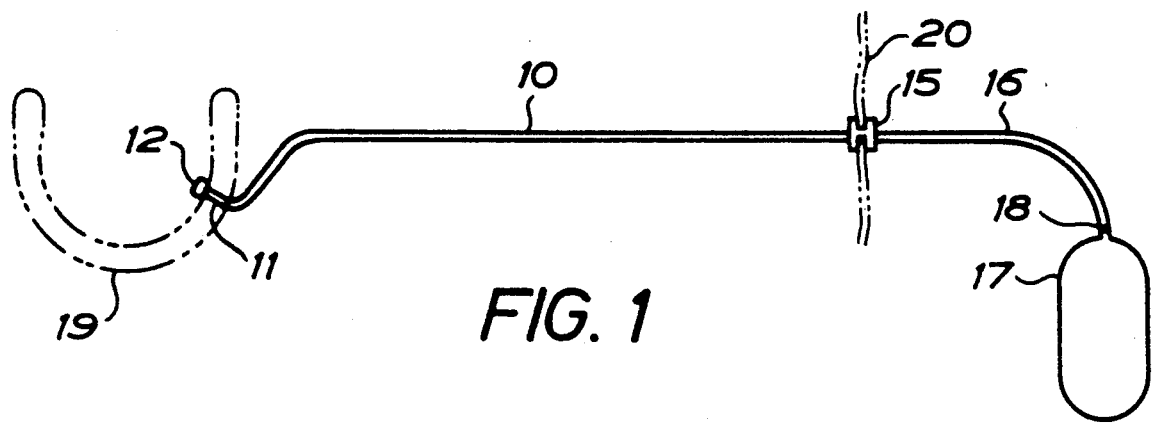

United States Patent [19]

Hakansson et al.

[11] Patent Number: 5,032,115
[45] Date of Patent: Jul. 16, 1991

[54] IMPLANTABLE DEVICE FOR THE SUPPLY OF A LIQUID TO THE ORAL CAVITY

[75] Inventors: Hakan Hakansson, Lund; Björn Klinge, Höllviken; Kare Larsson, Bjärred, all of Sweden

[73] Assignee: Bioimplant AB, Malmo, Sweden

[21] Appl. No.: 497,475

[22] Filed: Mar. 22, 1990

[30] Foreign Application Priority Data

Mar. 28, 1989 [SE] Sweden .............................. 8901058

[51] Int. Cl.$^5$ ............................................ A61M 31/00
[52] U.S. Cl. ............................ 604/142; 128/DIG. 12; 433/81; 604/153; 606/236
[58] Field of Search ............... 604/141, 142, 153, 132, 604/133; 606/234, 235, 236; 215/11.1, 11.2, 11.3, 11.4, 11.5, 11.6; 128/DIG. 12; 433/81, 224

[56] References Cited

U.S. PATENT DOCUMENTS

| | | | |
|---|---|---|---|
| 2,552,469 | 5/1951 | Wahlbeck et al. | 604/132 |
| 3,165,241 | 1/1965 | Curry | 215/11.1 |
| 3,506,005 | 4/1970 | Gilio et al. | 604/132 |
| 3,645,262 | 2/1972 | Harrigan | 215/11.1 |
| 4,090,514 | 5/1978 | Hinck et al. | 604/142 |
| 4,563,173 | 1/1986 | Ledley | 128/DIG. 12 |
| 4,796,628 | 1/1989 | Anderson | 606/236 |
| 4,898,290 | 2/1990 | Cueto | 215/11.1 |
| 4,936,831 | 6/1990 | Jaehrling et al. | 128/DIG. 12 |
| 4,955,860 | 9/1990 | Ruano | 128/DIG. 12 |

Primary Examiner—Paul J. Hirsch
Attorney, Agent, or Firm—Seidel, Gonda, Lavorgna & Monaco

[57] ABSTRACT

An implantable device for supplying liquid to the oral cavity comprises a liquid container having means for keeping the liquid under pressure, a tube, one end of which being connected to the container, said tube consisting of a material which is suitable for subcutaneous location in the human body, and an lead-through bushing connected to the other end of said tube, said bushing consisting of or being coated with a biocompatible material for being implanted into a jaw bone, and comprising a nozzle opening provided with a filter.

7 Claims, 2 Drawing Sheets

IMPLANTABLE DEVICE FOR THE SUPPLY OF A LIQUID TO THE ORAL CAVITY

The present invention relates to an implantable device for the supply of a liquid to the oral cavity.

Mouth aridity can occur in humans due to therapeutic treatment (with cell poisons or radiation) e.g. of cancer, or may be due to illness, for instance of the system desease called Sjögrens syndrome and which i.a. involves decreased secretion from the salivary glands and dry mucous membranes. The only remedy available today is to spray into the mouth a water solution, which then must be done in such short intervals as about 5 minutes. This interval can be increased up to about 15 minutes by adding to the water solution a chemical agent having surface tension changing properties, resulting in less evaporation of the water solution and a reduced reaction with the body tissues. It is easily imagined that the necessity of spraying the mouth once a quarter during sleep involves a great physical and mental strain, and it is also well known that mouth aridity is difficult to endure and often results in that the person suffering thereof tries to commit suicide.

The object of the invention is to provide a device enabling continuous removal of mouth aridity, particularly in order to give the patient the possibility of a continuous sleep, and which further renders possible that the treatment is carried out automatically and does not require repeated intervention by the patient.

For the purpose mentioned the device according to the invention has obtained the characterizing features appearing from claim 1.

Figure 2:
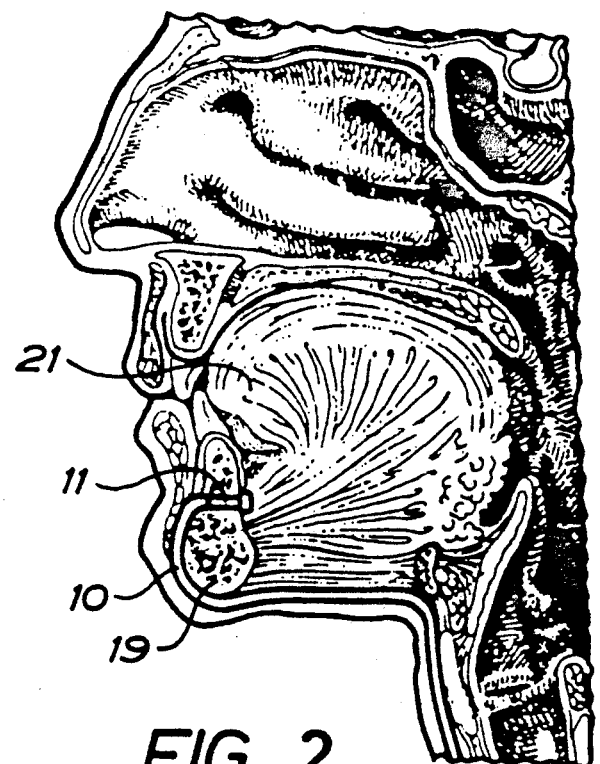
Figure 3:
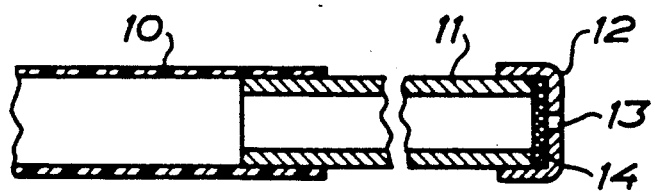
Figure 4:
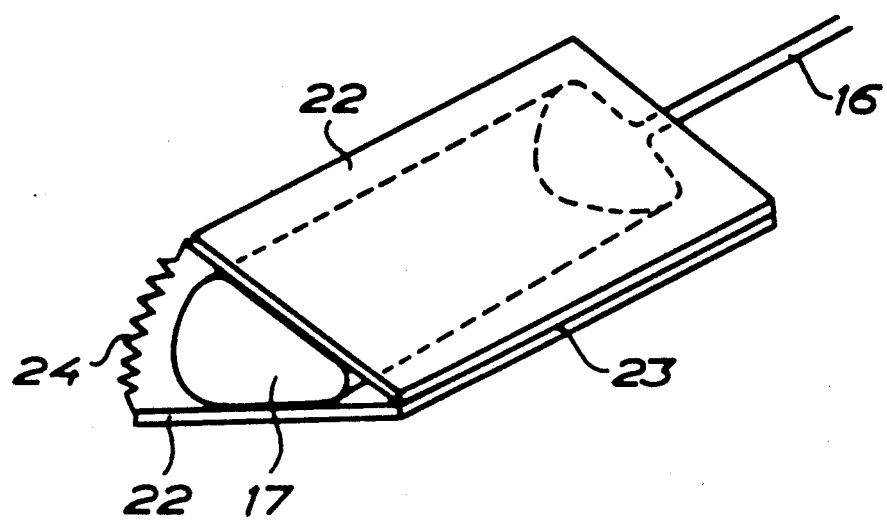
Figure 5:
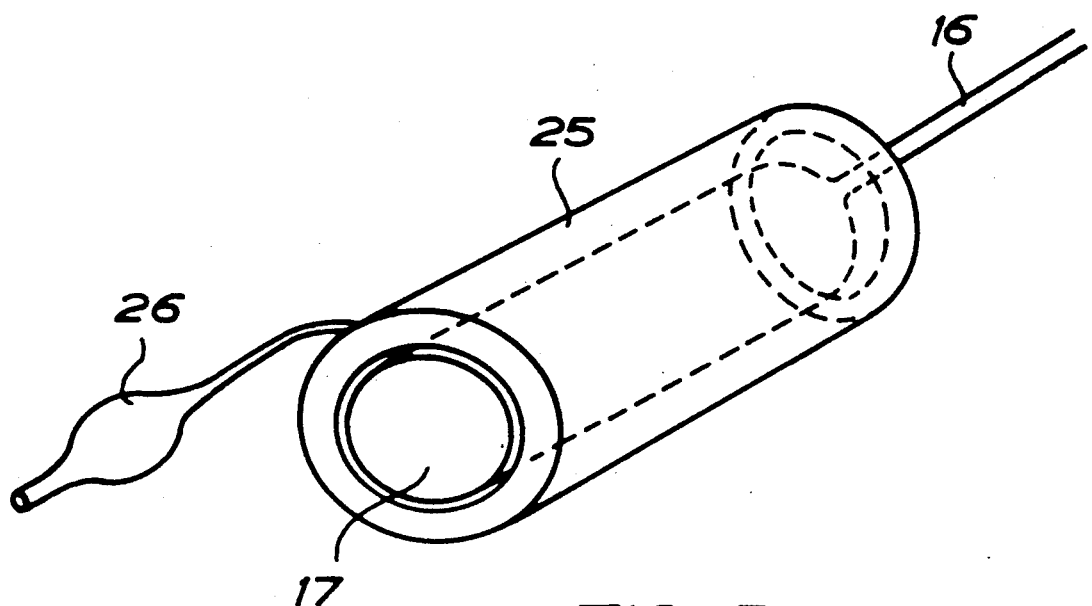

For providing a more detailed explanation of the invention an embodiment thereof will be described more closely below with reference to the appended drawing, in which FIG. 1 is a schematical illustration of the device according to the invention, FIG. 2 is a partial vertical cross sectional view of the human jaw portion with the device according to the invention surgically implanted in the lower jaw, FIG. 3 is an axial sectional view of the lead-through bushing and the end portion of the connected end tube, shown on an enlarged scale, FIG. 4 is a simplified perspective view of a container with pressurizing means of the spring type, and FIG. 5 is a simplified perspective view of a container with pressurizing means of the sleeve type.

FIG. 1 shows the device according to the invention in its entirety. It includes a tube 10 consisting of a biocompatable material, e.g. silicon rubber, for rendering possible a subcutaneous accomodation in the human body. One end of the tube is connected to a lead-through bushing 11 of a biocompatible and osseointegrative material, e.g. titanium or hydroxyapatite, or of any other material having a surface layer of biocompatible and osseo-integrative material, for enabling the cutaneous passageway to get firmly rooted in the bone tissue. FIG. 3 illustrates in more detail how this lead-through bushing is designed. The tube 10 is passed onto one end of the lead-through bushing and in a suitable manner attached thereon, e.g. by welding or gluing, while the other end of the bushing is provided with an attached hood 12 of a biocompatible material, e.g. a suitable plastic material. Externally said hood is gently rounded and is provided with a small central nozzle opening 13, and a filter disc 14 is attached between said hood and the end of the bushing.

The opposite end of the tube 10 is connected to an cutaneous passageway 15 of the type shown in the published international application No. WO 87/06122, on one side thereof, while the other side being connected with a plastic tube 16 leading to a soft container 17 for saliva substitute, e.g. a plastic bag. The tube or the opening portion of the plastic bag may be provided with a restriction 18, possibly adjustable.

In FIG. 1 the lower jaw bone of a human being is schematically indicated by dash-and-dot lines at 19, and as can bee seen the lead-through bushing passes through the jaw bone, the hood 12 being positioned on the inside of said jaw bone, while the tube 10 is connected to the lead-through bushing at the outside of the jaw bone. FIG. 1 also indicates by dash-and-dot lines 20 a skin portion in which the cutaneous passageway 15 is implanted. FIG. 2 shows in more detail the arrangement of the lead-through bushing in the jaw bone 19. A boring has been made right through the jaw bone from the outside thereof to the inside thereof, and the bushing is implanted in said boring in order to get firmly rooted therein. The hood 12 on the inside of the jaw bone is situated underneath the front portion of the tongue 21, the nozzle opening 13 communicating with the oral cavity. Due to the fact that the hood is gently rounded, it cannot have any irritating effect on the tongue. The tube 10 connected to the bushing at the outside of the jaw bone, is subcutaneously accomodated and in this manner drawn up to the cutaneous passageway 15, which is positioned at a suitable spot on the body in which the tube 16 with advantage may be connected for being extended externally on the body up to the container 17. The liquid within the container shall be kept under pressure, and this may be effected in any suitable manner. Illustrated here are pressurizing means of two different types which are suitable for this purpose. According to FIG. 4 said pressurizing means comprises two plates 22 which are a articulately interconnected at 23 along one edge, and at the opposite edge interconnected by means of a tension spring 24. The container (plastic bag) 17 is inserted between said two plates and is thus being held under pressure between said plates by means of the spring.

According to FIG. 5 said pressurizing means consists of an inflatable sleeve 25 of the type used in blood pressure testing. The sleeve is connected to an air pump 26 of the ball type by means of which said sleeve may be inflated for pressurizing the container 17 surrounded by the sleeve.

From the container 17 a suitable flow of saliva substitute is thus continuously supplied to the oral cavity through the tube 10 and the lead-through bushing 11 for being sprayed through the nozzle opening 13 into the oral cavity for wetting the mucous membranes thereof. This is effected without interference from the person having received the device according to the invention surgically implanted, which means that the inconveniences mentioned initially are eliminated. When the container is empty it can easily be exchanged. Due to the fact that the device is surgically implanted into the jaw bone with the tube extending subcutaneously up to the cutaneous passageway 15 positioned at a spot which is conventient to the patient, the patient may without harm carry the device without this one being externally noticeable.

In the drawing the lead-through bushing 11 in FIG. 2 is shown disposed right in front of the lower jaw, but as appears from FIG. 1 the bushing may be located at one side thereof, which may be more suitable since this location allows the tube more easily to be extended subcutaneously from the lead-through bushing.

We claim:

1. Implantable device for the supply of a liquid to the oral cavity comprising a liquid container, means for keeping liquid in said container under pressure, a tube, one end of which is connected to the container, said tube consisting of a material suitable for subcutaneous location in the human body, a lead-through bushing connected to the other end of said tube, the surface of said bushing being formed by a biocompatible material, to be implanted into a jaw bone and forming a nozzle opening, and a filter in said bushing.

2. Device as claimed in claim 1, wherein said bushing comprises a tube a hood attached at one end of said tube, and said filter being a filter disc clamped between the end surface of the tube and said hood, the nozzle opening being located in said hood.

3. Device as claimed in claim 1, wherein the lead-through bushing is made of an osseo-integrative material.

4. Device as claimed in claim 1, wherein the lead-through bushing is coated with an osseo-integrative material.

5. Device as claimed in claim 1, further comprising a cutaneous implant passageway connecting the tube to said container.

6. Device as claimed in claim 1, further comprising a restriction in the connection between the container and the tube.

7. Device as claimed in claim 1, wherein the container comprises a plastic bag, said means comprising compression means continuously exerting a pressure on the bag.

* * * * *